US00PP25886P3

(12) United States Plant Patent

Hansen et al.

(10) Patent No.: US PP25,886 P3

(45) Date of Patent: Sep. 8, 2015

(54) *AGASTACHE* PLANT NAMED 'PEACHIE KEEN'

(50) Latin Name: ***Agastache* spp.**
Varietal Denomination: Peachie Keen

(71) Applicants: Hans A. Hansen, Zeeland, MI (US); Kevin A. Hurd, Merrillville, IN (US)

(72) Inventors: Hans A. Hansen, Zeeland, MI (US); Kevin A. Hurd, Merrillville, IN (US)

(73) Assignee: Walters Gardens Inc, Zeeland, MI (US)

( * ) Notice: Subject to any disclaimer, the term of this patent is extended or adjusted under 35 U.S.C. 154(b) by 112 days.

(21) Appl. No.: 13/998,864

(22) Filed: Dec. 16, 2013

(65) Prior Publication Data

US 2015/0173286 P1 Jun. 18, 2015

(51) Int. Cl.
*A01H 5/02* (2006.01)

(52) U.S. Cl.
USPC ..... Plt./399

(58) Field of Classification Search
USPC ..... Plt./399
See application file for complete search history.

*Primary Examiner* — Susan McCormick Ewoldt

(57) ABSTRACT

A new and unique cultivar of *Agastache* plant, named 'Peachie Keen' with large peachy colored flowers in tightly clustered verticils. The plant habit is compact and upright with a long bloom time and usefulness in the landscape extended by the persistent and colorful mauve calyxes.

1 Drawing Sheet

Botanical denomination: *Agastache* spp.
Variety designation: 'Peachie Keen'.

BACKGROUND OF THE INVENTION

The present invention relates to the new and distinct plant cultivar of Hyssop or Anise Hyssop from the genus *Agastache* and given the cultivar name 'Peachie Keen' previously known internally by the breeder code HK-10-18-02. The new plant was the result of a planned cross in the summer of 2010 by Kevin A. Hurd and Hans A. Hansen between *Agastache* 'Firebird' (not patented) as the female or seed parent and *Agastache* 'Ava' (not patented) in a mixed isolation bed as the male or pollen parent. The seed was collected in September of 2010 and the new hybrid was first isolated from trials at a nursery in Zeeland, Mich. during the summer of 2011 and selected for final introduction in the summer of 2012. *Agastache* 'Peachie Keen' has been asexually propagated at the same nursery in Zeeland, Mich. using traditional shoot tip and stem cutting procedures and found to reproduce plants that are identical and exhibit all the characteristics of the original plant in successive generations of asexual propagation.

The new plant, *Agastache* 'Peachie Keen', has not been observed under all possible environments. The phenotype may vary slightly with different environmental conditions, such as temperature, light, fertility, moisture and maturity levels, but without any change in the genotype.

In comparison to the seed parent, *Agastache* 'Firebird', the new cultivar 'Peachie Keen' has peachy-colored flower petals rather than the reddish orange flower petals of 'Firebird', and the flower buds on 'Peachie Keen' are more orange and less red than the buds of 'Firebird'. In comparison to the male plant in the isolation bed, *Agastache* 'Ava', the new plant has flowers with much less red petals and calyxes with less intense red with a green undertone.

The new plant *Agastache* 'Peachie Keen' is distinct from the parents and all other Hyssop known to the inventors in the following combined traits:

1. Compact upright well-branched habit;
2. Large peachy-colored flowers in tightly clustered verticils;
3. Long bloom time with effectiveness extended by persistent mauve-colored calyxes.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED PLANT DESCRIPTION

Figure 1:
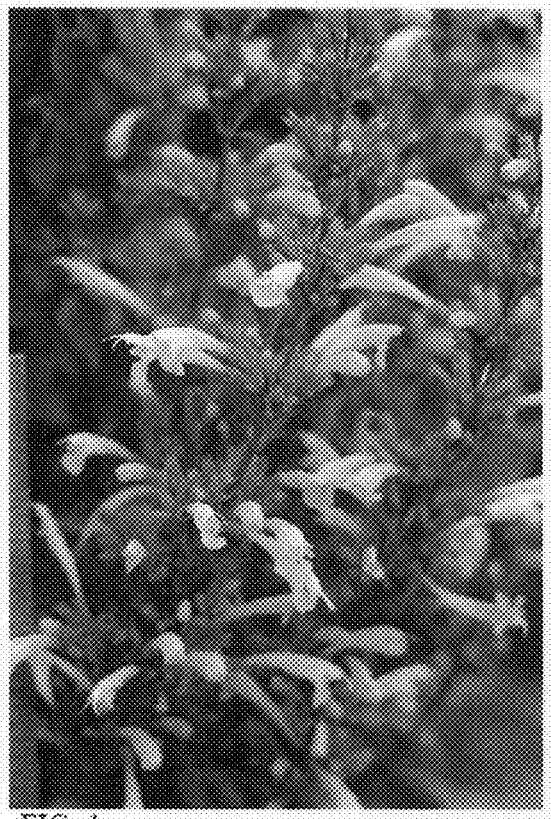
FIG. 1 shows a close-up of the scape with flowers, buds and calyxes.
Figure 2:
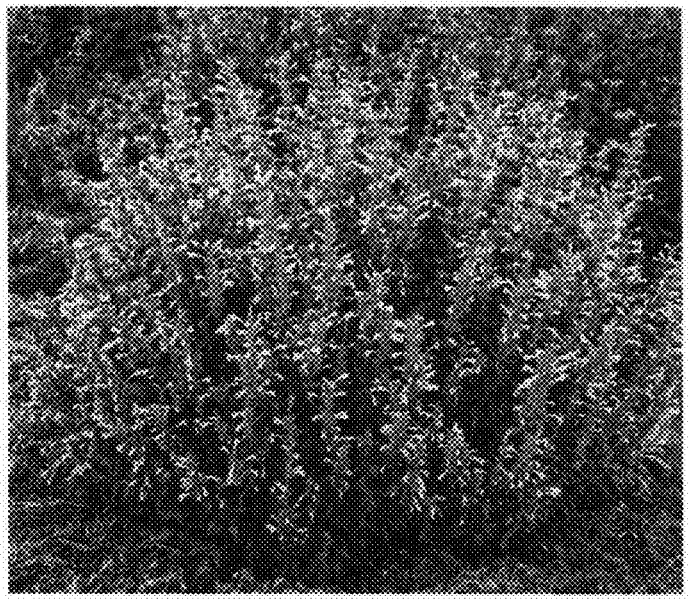
FIG. 2 shows a side view of a two-year old plant in flower in mid-September in a trial block at a nursery in Zeeland, Mich.

The following is a detailed description of the new *Agastache* cultivar 'Peachie Keen' based on observations of two-year old specimens grown in outdoor trial beds with supplemental watering and fertilizer as needed at a nursery in Zeeland, Mich. Color descriptions are from the 2001 edition of The Royal Horticultural Society Colour Chart except where common dictionary terms are used.

Plant habit: Herbaceous perennial, upright, heavily branched.
Plant size: 43.0 to 47.0 cm tall and 45.0 to 48.0 cm across.
Roots: Fibrous; to about 2.0 mm diameter near base; color light tan nearest RHS 165D varying with soil type.
Stem: Stiff, wiry, finely pubescent, square in cross-section; averaging about 3.0 mm across at base and 45.0 cm tall with flowering starting about 10.0 cm above soil; internodes vary from 2.0 to 5.0 cm long.

Leaf: Simple, opposite, crenate to serrate; deltoid to ovate, base truncate to rounded with acute apex; blade top and bottom surfaces glabrous; size 3.5 cm to 6.5 cm long and 1.7 to 3.5 cm across, average about 4.0 cm long and 1.8 cm wide.

Leaf venation: Pinnate; glabrous above, pubescent below.

Leaf color: Above nearest RHS 137A, below nearest RHS 138A; veins above the same color as surrounding tissue, below nearest RHS 138B; young developing leaves with underside of nearest RHS 187A.

Leaf fragrance: Moderately herbal.

Petiole: Minutely pubescent; concavo-convex; 0.5 cm to 1.2 cm long and 1.0 to 1.5 mm across.

Petiole color: Above nearest RHS 137A, below nearest RHS 138B.

Inflorescence: In spikes with verticils in leaf axils and nodes above leaves; 5 to 15 whorls per spike; up to 35 flowers per verticil and about 230 per spike.

Bloom period: July through frost in Zeeland, Mich.

Peduncle: Average 45.0 cm tall and 3.0 mm at base; finely pubescent.

Peduncle color: Between RHS 138A and RHS 144A in upper portion of stem; node color and lower regions of young developing stems tinted nearest RHS N187B.

Flower: Perfect; zygomorphic, tubular, bilabiate; in spikes and whorls in axils of leaves; 5 united sepals, 5-part corolla with 2 lips, upper lip 2-lobed and lower lip 3-lobed; about 2.5 cm long, 7.0 mm tall and 6.0 mm across; each spike flowering for about 3 weeks but remain effective for about 5 weeks or more with strongly pigmented persistent calyxes, individual flowers open for about 2 to 3 days.

Petals: Pubescent outside, glabrous inside; upper and lower petals proximally fused to a tube in the basal 16.0 mm.

Upper 2-lobed petal: About 22.0 mm long and 5.0 mm diameter; lobes cleft about 1.5 mm deep; apex rounded, margin entire.

Lower 3-lobed petal: About 23.0 mm long, bent downward in last 6.0 mm, central lower lip about 4.0 mm wide at base of three lobes reflex downward and flares to about 7.0 mm wide with a rounded apex and serrate margin; two side lobes of lower petal spread horizontally, about 18.0 mm long with broadly acute apex and entire margin.

Petal color: Abaxial and adaxial surfaces between RHS 22B and RHS 23C.

Bud one day prior to opening: Club-shaped to obelliptic; about 17.0 mm long, 6.0 mm tall and 4.5 mm wide just before the distal end.

Bud color: Between RHS 23B and RHS 23A distally, lightening to nearest RHS 23C toward base.

Calyx: Five, distally separated in last 1.5 mm and fused in basal 6.5 mm; entire, apex acute, base fused into tube; about 8.0 mm long and 2.5 mm diameter; pubescent outside and glabrous inside.

Calyx color: Young opened flowers nearest RHS 27D, flowers open for a few days lighter and more yellow than RHS 27D and lighter and more pinkish than RHS 20D.

Gynoecium:

*Style.*—One, about 20.0 mm long and 0.5 mm diameter; round in cross section; color nearest RHS 155D at base and RHS 29C distally before stigma; Stigma; one split and curled back over 180 degrees in last 1.5 mm; color nearest RHS 187D; Ovary; superior; color between RHS 150 D and RHS 150C.

Androecium:

*Stamen.*—Four in two pairs, exerted; adnate to corolla.

*Filaments.*—Two long and two short; longer pair fused in the basal 17.0 mm and free in the proximal 8.0 mm; shorter pair fused in the basal 14.0 mm and free in the proximal 8.0 mm; color nearest RHS 18B.

*Anther.*—Dorsifixed, versatile, longitudinal; about 1.0 mm long and 0.5 mm across; color nearest RHS N186C.

Fruit: Two carpels.

Seed: Nutlet; four; flattened ovoid; about 2.0 mm long, 1.0 mm diameter and 0.5 mm thick; color nearest RHS 202A.

Fragrance: None detected from flower.

Resistance: 'Peachie Keen' is resistant to deer browsing but has not been tested or shown resistance to other pests and diseases common to *Agastache*. The new plant has survived USDA hardiness zones 7 to 10 but has not been tested yet beyond these temperatures.

We claim:

1. The new and distinct plant cultivar *Agastache* 'Peachie Keen' as herein described and photographed, with compact upright habit, large peachy-colored flowers in tightly clustered verticils, and long effective bloom time, for cut flowers, for landscaping and attracting butterflies as well as hummingbirds.

* * * * *